US011399849B2

(12) United States Patent
Larche et al.

(10) Patent No.: US 11,399,849 B2
(45) Date of Patent: Aug. 2, 2022

(54) SURGICAL GUIDE DEVICE FOR ASSISTING AN OPEN WEDGE OSTEOTOMY

(71) Applicant: NEWCLIP INTERNATIONAL, Luxembourg (LU)

(72) Inventors: Grégoire Larche, Cholet (FR); Jean-Pierre Podgorski, St-Crespin sur Moine (FR); Frank Baudry, Pornichet (FR); Philippe Berton, Aix en Provence (FR)

(73) Assignee: NEWCLIP INTERNATIONAL, Luxembourg (LU)

( * ) Notice: Subject to any disclaimer, the term of this patent is extended or adjusted under 35 U.S.C. 154(b) by 67 days.

(21) Appl. No.: 16/640,888

(22) PCT Filed: Aug. 20, 2018

(86) PCT No.: PCT/EP2018/072461
§ 371 (c)(1),
(2) Date: Feb. 21, 2020

(87) PCT Pub. No.: WO2019/038240
PCT Pub. Date: Feb. 28, 2019

(65) Prior Publication Data
US 2020/0352582 A1    Nov. 12, 2020

(30) Foreign Application Priority Data
Aug. 22, 2017 (FR) ........................................ 1757798

(51) Int. Cl.
*A61B 17/17* (2006.01)
*A61B 17/80* (2006.01)
(Continued)

(52) U.S. Cl.
CPC ...... *A61B 17/1764* (2013.01); *A61B 17/8095* (2013.01); *A61B 17/864* (2013.01); *A61B 2017/00526* (2013.01)

(58) Field of Classification Search
CPC . A61B 17/151; A61B 17/152; A61B 17/1728; A61B 17/1764; A61B 17/8095
See application file for complete search history.

(56) References Cited

U.S. PATENT DOCUMENTS 5,078,719 A * 1/1992 Schreiber ............. A61B 17/152
606/87
5,935,128 A * 8/1999 Carter .................. A61B 17/151
606/86 B
(Continued)

FOREIGN PATENT DOCUMENTS

AU   2014262239 A1   12/2014
WO   2011/001292 A1   1/2011
(Continued)

OTHER PUBLICATIONS

Extended European Search Report issued in European Patent Application No. 20212300.6 dated Mar. 15, 2021.
(Continued)

*Primary Examiner* — Samuel S Hanna
(74) *Attorney, Agent, or Firm* — Nixon & Vanderhye

(57) ABSTRACT

A surgical guide device can be attached to a patient's bone for assisting an open wedge osteotomy. This device includes two parts which are joined together by way of removable securing unit, namely: a proximal part, including a lower border defining at least one portion of the upper edge of a guide window, and a distal part having an upper edge defining at least one portion of the lower edge of the guide window. The proximal and distal parts are each provided with a plurality of through holes adapted for receiving members temporarily implantable in the bone and/or
(Continued)

adapted to guide a drilling of holes in the bone. The arrangement of the through holes of the surgical guide device advantageously takes into account the planned open wedge osteotomy and anticipates the final position of the screw locations of the reported osteosynthesis plate for freezing the two bone fragments.

12 Claims, 5 Drawing Sheets

(51) Int. Cl.
  *A61B 17/86* (2006.01)
  *A61B 17/00* (2006.01)

(56) References Cited

U.S. PATENT DOCUMENTS

| | | |
|---|---|---|
| 2004/0260301 A1 | 12/2004 | Lionberger et al. |
| 2009/0254126 A1 | 10/2009 | Orbay et al. |
| 2011/0213376 A1 | 9/2011 | Msxon et al. |
| 2014/0074101 A1 | 3/2014 | Collazo |
| 2016/0066930 A1* | 3/2016 | Geeblen .............. A61B 17/1764 606/88 |
| 2016/0235454 A1* | 8/2016 | Treace ................ A61B 17/8863 |
| 2017/0360453 A1* | 12/2017 | Brailovski ............. A61B 17/15 |

FOREIGN PATENT DOCUMENTS

| | | |
|---|---|---|
| WO | 2016/033497 A1 | 3/2016 |
| WO | 2017/070318 A1 | 4/2017 |

OTHER PUBLICATIONS

International Search Report, dated Nov. 23, 2018, from corresponding PCT application No. PCT/EP2018/072461.

* cited by examiner

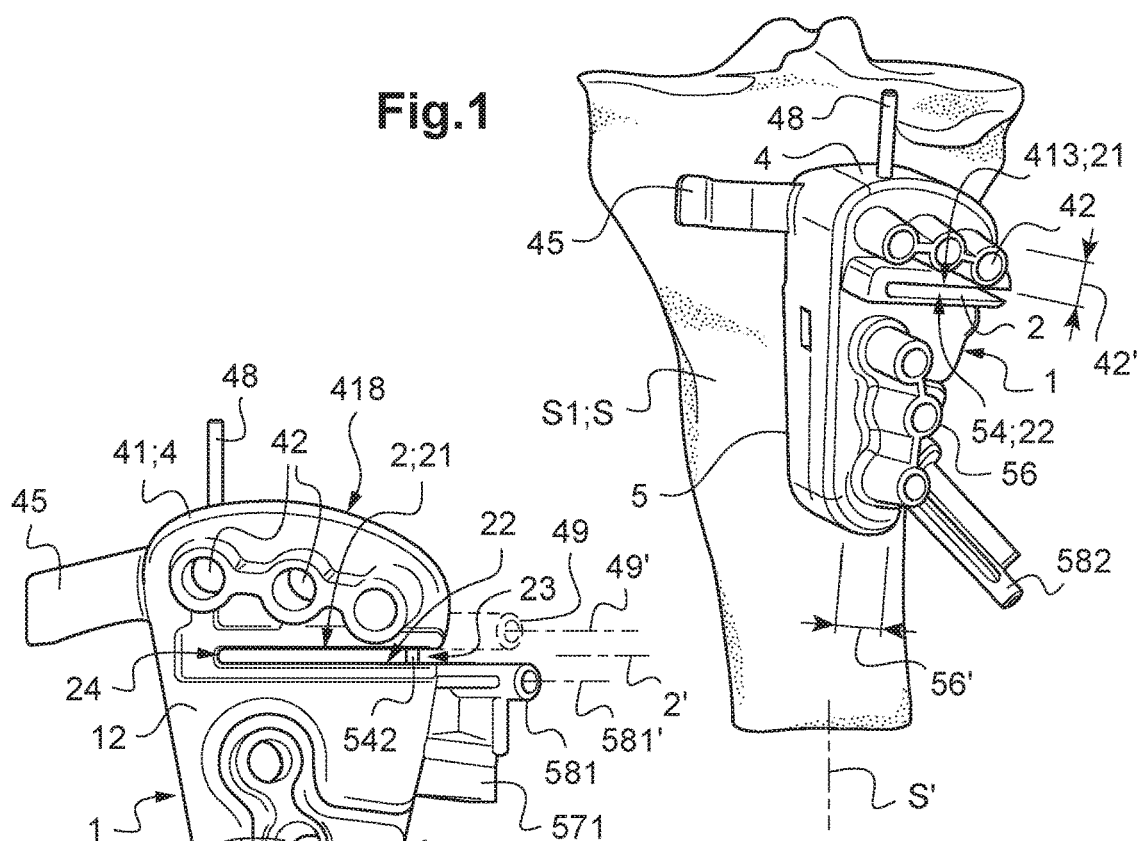
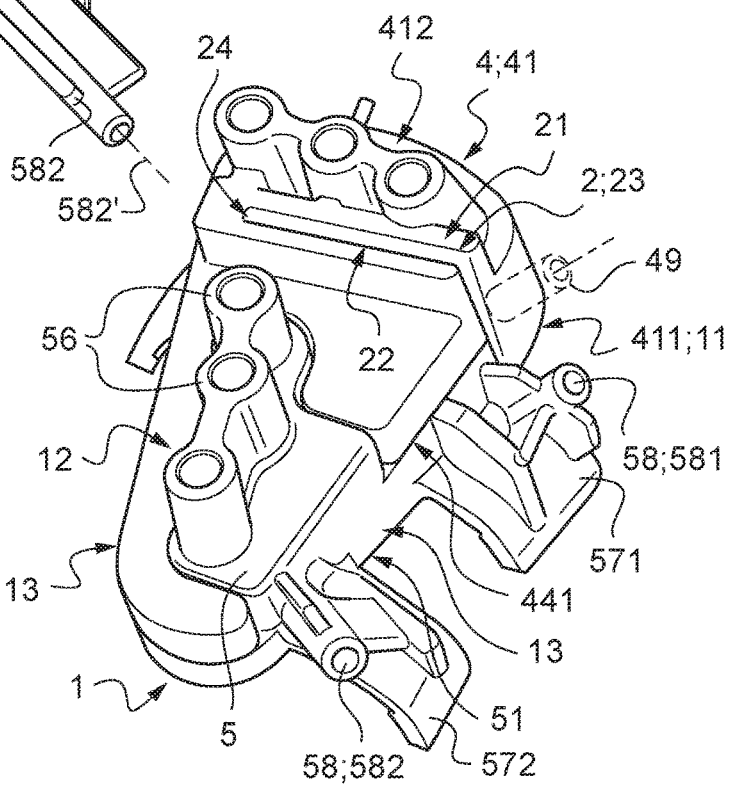

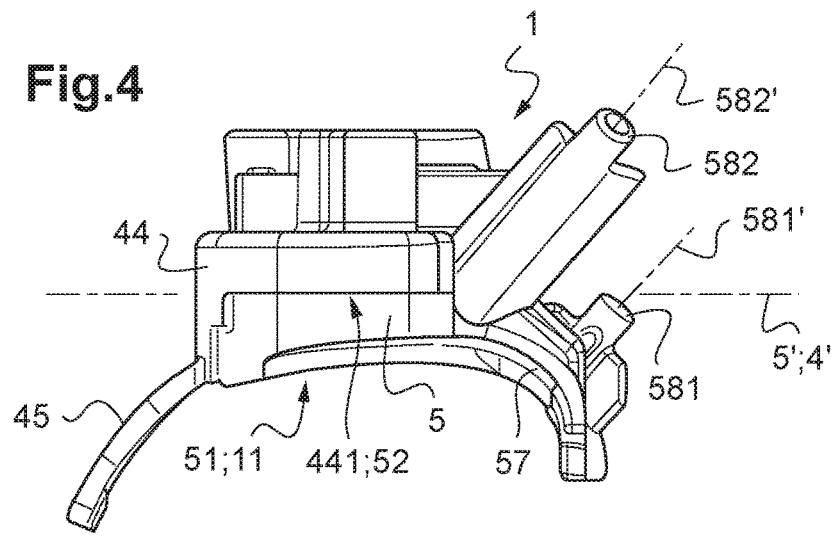
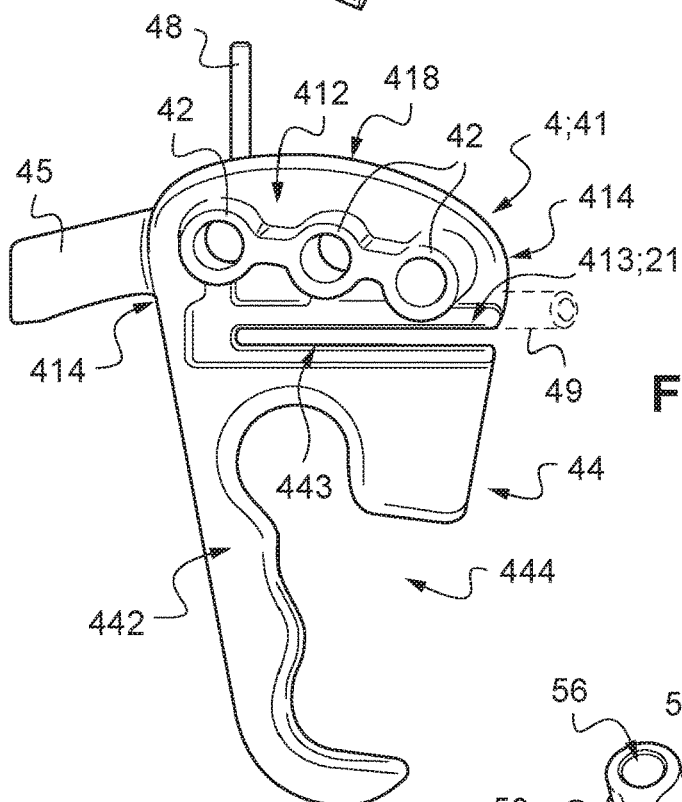
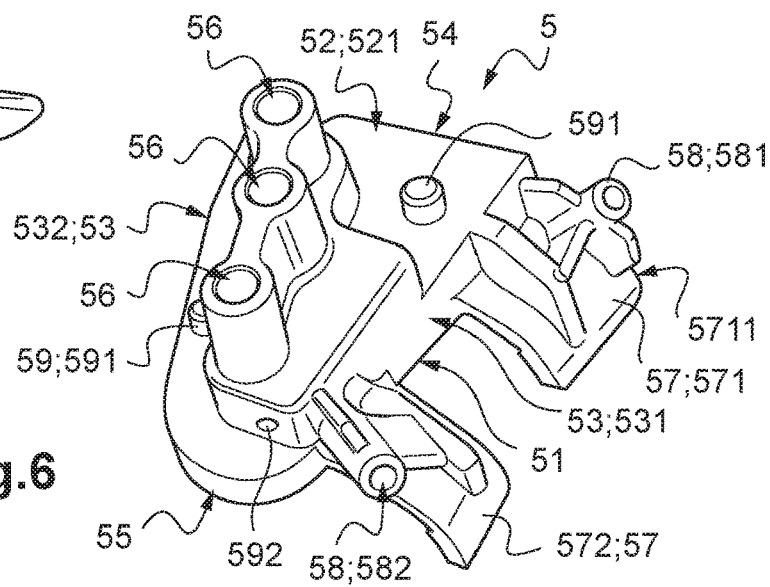

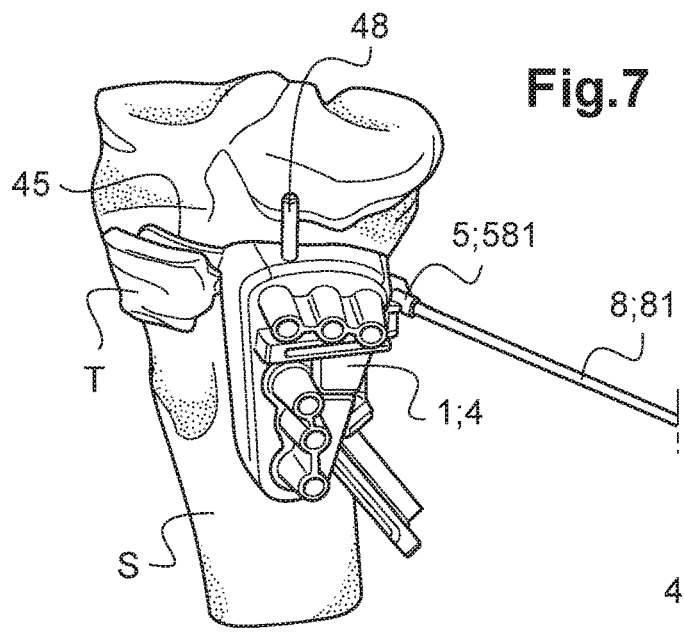
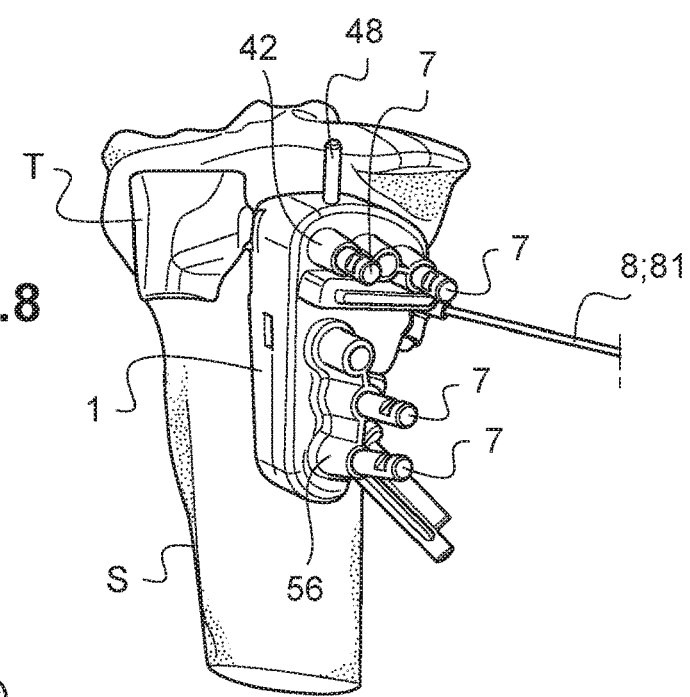
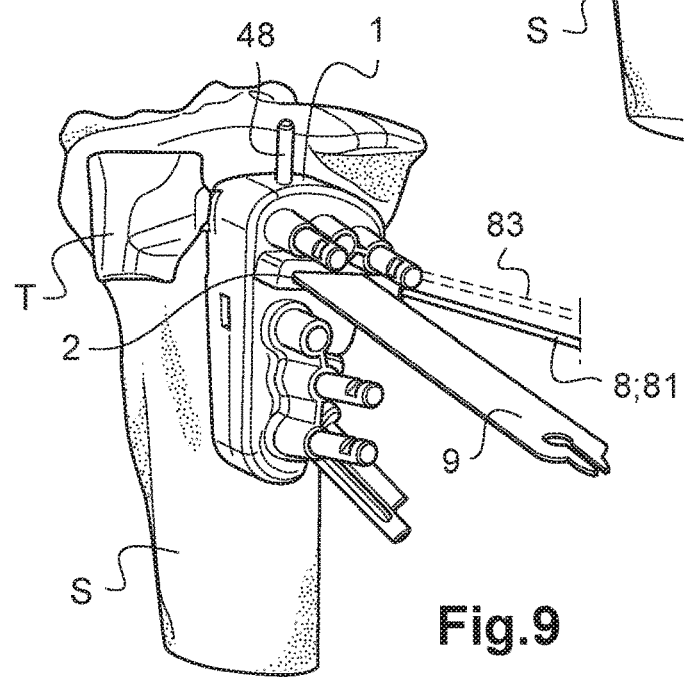

SURGICAL GUIDE DEVICE FOR ASSISTING AN OPEN WEDGE OSTEOTOMY

TECHNICAL FIELD TO WHICH THE INVENTION RELATES

The present invention generally relates to the field of orthopaedic surgery.

It more particularly relates to the surgical devices intended to assist the opening wedge osteotomy techniques.

TECHNOLOGICAL BACK-GROUND

Osteotomy is the surgical cutting of a long bone, to modify the axis, size or shape thereof, for therapeutic or plastic purposes.

Among the osteotomy techniques, the so-called "opening wedge osteotomy" techniques can in particular be mentioned, which consist in cutting the bone to be treated by a cut line, then in spacing apart the edges of the line by introducing therein a wedge made of bone or of an artificial material (metal, cement, bone substitute).

Once the correction obtained, the two bone fragments are firmly maintained by an osteosynthesis material, in particular an osteosynthesis plate held by screws.

Such a surgical operation is for example useful to treat certain arthroses localized at the knee, in order to correct a deformation of the lower limb and to obtain a tibial alignment correction. In particular, the tibial valgus osteotomy remains an operation of choice for treating in internal femorotibial arthritis on a genu varum.

The preoperative planning is essential in this type of operation, in particular to determine accurately the value of the spatial correction that will have to be made through the opening (in particular, HKA angle and tibial slope). But, to date, this planning remains a difficult practice in which operator's experience and empiricism are of high importance in the success of the operation.

Likewise, during the operation, it is often difficult for the surgeon to scrupulously follow the preoperative planning file, in particular as regards the arrangement of the cut line and of the osteosynthesis plate.

It hence exists a need for means providing assistance to the operator all along the opening wedge osteotomy operation, so as to efficiently follow the preoperative planning.

OBJECT OF THE INVENTION

In order to remedy the above-mentioned drawback of the state of the art, the present invention proposes a surgical guide device, intended to be placed against a patient's bone, for assisting an opening wedge osteotomy technique.

This surgical guide device comprises:—a rear face adapted to be positioned against a surface of said bone, and—a window for guiding a cut line intended to be made into said bone.

The guide window is delimited by an upper edge and a lower edge, arranged opposite to each other and spaced apart from each other.

And this surgical guide device comprises two parts that are assembled to each other through detachable fastening means, i.e.:
  a proximal part, having a lower edge defining at least one portion of said upper edge of said guide window, and
  a distal part, having an upper edge defining at least one portion of said lower edge of said guide window.

The proximal and distal parts are each provided with several through-orifices opening through said rear face, adapted to guide a drilling of holes into said bone, and possibly adapted to receive elements temporarily implantable into said bone.

Such a surgical guide device has hence for interest to assist the operator during the opening wedge osteotomy operation, so as to precisely follow the preoperative planning.

As developed hereinafter, the arrangement of the through-orifices of the surgical guide device takes into account the opening wedge osteotomy technique that has been planned and previously simulated via scanner acquisition with a three-dimensional reconstruction of the anatomic region to be corrected.

This approach hence allows anticipating:
  the final position of the screw locations in the osteosynthesis plate placed so as to freeze the two bone fragments, and
  the spatial position of the bone cut line to be made to generate the desired opening.

The surgical guide device hence advantageously consists of a Patient Specific Instrument (PSI). The design of this instrument uses the imaging technologies and preoperative planning tools for its custom manufacturing, taking into account the unique anatomy of each patient.

This surgical guide device hence helps the surgeon to perform operations in a precise and secure manner.

Other non-limitative and advantageous features of the surgical guide device according to the invention, taken individually or according to all the technically possible combinations, are the following:
  the surgical guide device has two lateral edges, at least one of which comprises at least one tab adapted to be positioned against a surface of said bone, wherein said tab has an ability of elastic deformation;
  the proximal part comprises at least two through-orifices, juxtaposed and independent of each other, that extend in a virtual strip intended to be directed transversally with respect to the longitudinal axis of the bone;
  the proximal part is provided with an upper protrusion, having preferentially the shape of radio-opaque cylindrical dog point, intended to help the practitioner to correctly position the guide at the good distance with respect to the patient's tibial plateau;
  the proximal part also comprises a tubular duct that is adapted to guide the insertion of a rod within the bone, wherein said tubular duct is formed directly overlying the guide window and is directed in such a manner that its longitudinal axis is parallel to the plane of the guide window in order to position a rod helping in the guiding of the cut line;
  the distal part comprises at least two through-orifices, juxtaposed and independent of each other, extending in a virtual strip that is at least approximately perpendicular to the virtual strip followed with the orifices of the proximal part and that is intended to be directed at least approximately parallel to the longitudinal axis of the bone;
  the distal part comprises at least one through-orifice in the form of a tubular duct, which is adapted to guide the insertion of a rod within the bone: a proximal tubular duct that is arranged directly underlying the guide window and that is directed in such a manner that its longitudinal axis is parallel to the plane of the guide window in order to position a rod helping in the guiding of the cut line, and/or a distal tubular duct that is arranged remote from the guide window and that is directed in such a manner that its longitudinal axis intersects the plane of the guide window in order to position a cut stop and/or hinge indication rod; according to a particular embodiment, the distal part comprises at least two distal tubular ducts that are arranged remote from the guide window and that are directed in such a manner that their respective longitudinal axes intersect the plane of the guide window in order to each position a cut stop and/or hinge indication rod;

the surgical guide device is made of a plastic material adapted to the additive manufacturing and to an invasive use within the human body.

The invention also proposes equipment for implementing an opening wedge osteotomy technique, that comprises:

a surgical guide device according to the invention, elements temporarily implantable into the bone, through the through-orifices of said surgical guide device, as the case may be, rods temporarily implantable into the bone, through the through-ducts of said surgical guide device, a cutting blade, for making the cut line guided by the surgical guide device, an osteosynthesis plate provided with two groups of through-orifices, a proximal one and a distal one, each of said groups of orifices being intended to receive fastening screws intended to be implanted into one of the two bone fragments, a set of screws for the fastening to the bone, intended to be inserted through the through-orifices of said osteosynthesis plate to fasten the latter to the surface of the bone.

Within this framework, the arrangement of the through-orifices of the proximal part corresponds to the arrangement of the proximal through-orifices of the osteosynthesis plate; and the arrangement of the through-orifices of the distal part corresponds to the arrangement of the distal through-orifices of the osteosynthesis plate.

And the relative arrangement between the two groups of through-orifices of the surgical guide device is function, on the one hand, of the correction intended to be applied during the opening wedge osteotomy technique and, on the other hand, of the relative arrangement of the two groups of through-orifices of the osteosynthesis plate, in order to obtain the desired correction when the orifices formed in the bone come into alignment with those arranged in the plate at the end of the osteotomy site opening process.

The invention also relates to a method for obtaining a surgical guide device according to the invention.

This method comprises:

a) a step of simulating the correction intended to be applied to a bone by an opening wedge osteotomy technique, from the following data:

anatomic data taken on the bone to be treated, data relating to the osteosynthesis plate to be installed, and preoperative planning data, relating to the correction intended to be applied to this bone by the opening wedge osteotomy technique, and b) a step of manufacturing the surgical guide device, taking into account the correction data coming from said simulation step.

According to an advantageous feature, the step of manufacturing said surgical guide device consists of a step of additive manufacturing.

The invention also relates to a computer program comprising program code means recorded on a computer-readable medium, comprising:

first program code means, for loading data relating to the correction intended to be applied to a bone by an opening wedge osteotomy technique, from anatomic data relating to said bone and from data relating to the final position of the screws for fastening the osteosynthesis plate to the bone, second program code means, for generating manufacturing data relating to the surgical guide device, wherein said manufacturing data contain data relating to the arrangement of the through-orifices of the surgical guide device taking into account said correction data and said screw final position data, when said computer program is executed by a computer.

The invention also relates to a surgical method of opening wedge osteotomy, wherein said surgical method comprises:

a) a preparation step, during which the surgical guide device is fastened against the surface of the bone, and holes are generated into said bone opposite each of the through-orifices of said surgical guide device (with, possibly, the positioning of at least one lower rod arranged to intersect the hinge of the osteotomy site);

b) a bone osteotomy step, comprising:

a first cutting phase within the guide window of the surgical guide device, a removal of the proximal part of the surgical guide device, and a second cutting phase, leaning on the distal part of the surgical guide device;

c) a step of removing the distal part of the surgical guide device;

d) a step of fastening the osteosynthesis plate against a distal fragment of the bone, underlying the cut line, wherein said osteosynthesis plate is arranged so that the through-orifices thereof come opposite holes generated at step a), which are formed in said distal fragment;

e) a step of progressively opening the osteotomy site, until obtaining the desired correction corresponding to a matching of holes generated at step a), which are formed in a proximal fragment of the bone and overlying the cut line, with through-orifices of said osteosynthesis plate; and f) a step of fastening the osteosynthesis plate against the proximal fragment of the bone.

DETAILED DESCRIPTION OF AN EXEMPLARY EMBODIMENT

The following description with respect to the appended drawings, given by way of non-limitative examples, will permit a good understanding of what the invention consists in and of how it can be implemented.

In the appended drawings:

FIG. 1 is an overall and perspective view of a surgical guide device according to the invention, placed against a patient's bone intended to undergo an opening wedge osteotomy technique;

FIG. 2 is a front view of the surgical guide device illustrated in FIG. 1;

FIG. 3 is a perspective view of the surgical guide device illustrated in FIGS. 1 and 2;

FIG. 4 is a bottom view of the surgical guide device of FIGS. 1 to 3.

FIG. 5 is a front view of a proximal part of the surgical guide device of FIGS. 1 to 4, intended to cooperate with a first bone fragment;

FIG. 6 is a perspective view of a distal part of the surgical guide device of FIGS. 1 to 4, intended to cooperate with a second bone fragment;

FIGS. 7 to 13 represent the main steps of implementation of the surgical guide device, within the framework of a surgical operation of opening wedge osteotomy;

Figure 10:
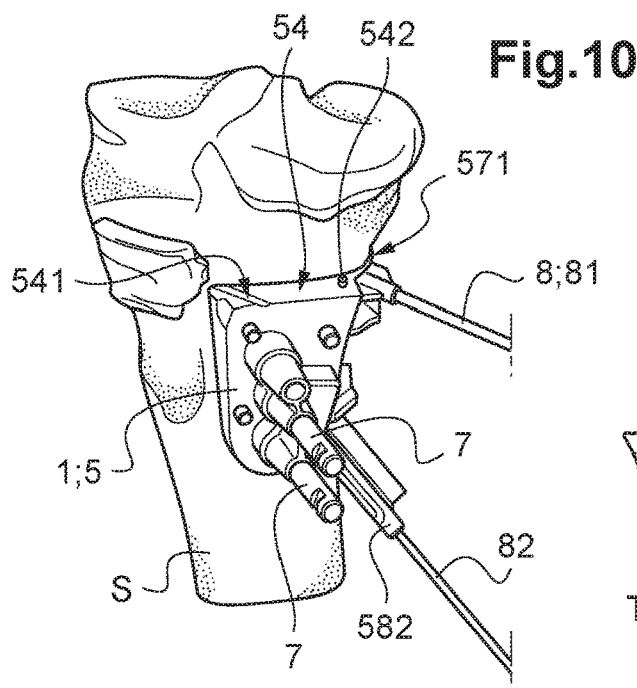

As shown in particular in FIG. 1, the surgical guide device 1 is intended to be placed against a patient's bone S, for assisting the surgeon during an opening wedge osteotomy technique.

By "opening wedge osteotomy", it is meant a surgical operation consisting in cutting a bone of the patient by a cut line, then in spacing apart the edges of the line by introducing therein a wedge made of bone or of an artificial material (metal, cement, bone substitute).

This surgical technique may be used to treat different bones of the human body.

Such a surgical operation is for example useful to treat certain arthroses localized at the knee, in order to correct a deformation of the lower limb and to obtain a tibial alignment correction. In particular, the tibial valgus osteotomy remains an operation of choice for treating in internal femorotibial arthritis on a genu varum.

Generally, the bone S to be treated has a surface S1; and this bone S also has a longitudinal axis S'.

Surgical Guide Device

The surgical guide device 1, shown in more detail in FIGS. 1 to 4, has the general form of a block.

This surgical guide device 1 (also called "guide") comprises a set of faces:
a rear face 11, adapted to be positioned against a surface S1 of the bone S to be treated,
a front face 12, located at the opposite of said rear face 11, and
two lateral faces 13, i.e.: a first lateral face 131 (posterior) and a second lateral face 132 (anterior).

This surgical guide device 1 also comprises a slot-shaped window 2 for guiding the cut line intended to be made into the bone S.

This guide window 2 is delimited by an upper edge 21 and a lower edge 22, arranged opposite to each other and spaced apart from each other.

These two edges 21 and 22 are rectilinear. They extend parallel to each other, defining together a general plane 2' (FIG. 2).

The distance between the two edges 21, 22 advantageously corresponds to the thickness of the cutting blade (to within the working clearance).

The thickness of the edges 21, 22 (between the rear 11 and front 12 faces) is advantageously comprised between 0.8 mm and 1.6 mm.

The guide window 2 is a through-window, i.e. it opens through the rear 11 and front 12 faces of the surgical guide device 2.

This guide window 2 is moreover laterally open on only one side, at a lateral opening 23 located in the first lateral face 131 of the surgical guide device 1.

The guide window 2 also comprises a lateral edge 24, forming a bottom, that extends between the two edges 21, 22 and that is located opposite the lateral opening 23.

The surgical guide device 1 herein comprises two parts 4, 5 that are assembled to each other by means of removable fastening means.

More precisely, this surgical guide device 1 comprises a first part 4, also called proximal part or portion (FIG. 5), and a second part 5, also called distal part or portion (FIG. 6).

These two parts 4, 5 are intended to each cooperate with one of the two bone fragments intended to be generated by the cut line made into the bone S through the guide window 2.

As described in more detail hereinafter, these two parts 4, 5 are each provided with several through-orifices that are adapted to receive elements temporarily implantable into the bone S and/or to guide a drilling of holes into this bone S.

Each of these parts 4, 5 is advantageously made single-piece in a plastic material adapted to the techniques of additive manufacturing (also called "3D printing" or "three-dimensional printing").

This plastic material is for example chosen among polyamides.

First Part

The first part 4 (proximal part), shown in more detail and in isolation in FIG. 5, comprises an upper portion 41 that has:
a rear face 411, intended to form an upper portion of the rear face 11 of the surgical guide device 1 (FIG. 3), and
a front face 412, intended to form an upper portion of the front face 12 of the surgical guide device 1.

The upper portion 41 comprises several through-orifices 42, opening through the rear 411 and front 412 faces thereof.

The through-orifices 42, also called "proximal through-orifices", are adapted to receive elements temporarily implantable into the bone S and/or to guide a drilling of holes into this bone S.

Herein, these through-orifices 42 are intended in particular to serve as a guide for drilling holes into a proximal fragment of the bone in order to facilitate the latter assembly of the osteosynthesis plate.

The juxtaposed through-orifices 42 are at least two in number (herein, three in number).

These through-orifices 42 extend in a virtual strip 42' intended to be directed transversally to the longitudinal axis S' of the bone S (FIG. 1).

This upper portion 41 comprises a lower edge 413, intended to form the upper edge 21 of the guide window 2.

This upper portion 41 is also delimited by two lateral edges 414 forming an upper portion of the lateral faces 13 of the surgical guide device 1.

One of these lateral edges 414 herein comprises a lateral tab 45 (anterior tab) that is adapted to be positioned against a surface of the bone S, as developed herein in relation with FIGS. 7 to 13.

The tab 45 has an ability of elastic deformation, so as to optimally conforms the surface of the bone S.

This tab 45 extends approximately parallel to the lower edge 413 and on the side of the rear face 411 of the upper portion 41 (FIG. 4). Its rear face approximately corresponds to the anatomic surface of the bone intended to be covered by it.

The upper portion 41 is herein extended by a lower portion 44 that is intended to cooperate with the second part 5, for the detachable assembly thereof.

The lower portion 44 is in the general form of a platen intended to conform a complementary recess formed in the front face of the second part 5.

This lower portion 44 then comprises:
- a rear face 441, intended to cover the second part 5 of the surgical guide device 1 (FIG. 3), and
- a front face 442, intended to form a portion of the front face 12 of the surgical guide device 1.

The rear face 441 of the lower portion 44 is set back with respect to the rear face 411 of the upper portion 41.

This lower portion 44 is herein also delimited by an upper edge 443 that is intended to form a portion of the lower edge 22 and the lateral edge 24 of the guide window 2, in particular intended to form the front portion of this lower edge 22.

This lower portion 44 also comprises an aperture 444, within which a complementary shape of the second part 5, in particular a portion comprising the through-orifices of this second part 5, are intended to be seated.

The proximal part 4 is also provided with an upper protrusion 48 that is intended to help the practitioner to correctly position the surgical guide device 1 at the good distance with respect to the patient's tibial plateau (checking of the guide 1 altitude).

This upper protrusion 48 is placed, herein removably, at an upper (free) face 418 of the upper portion 41.

This upper protrusion 48 has preferentially the shape of a radio-opaque cylindrical dog point (also called stem or rod).

Moreover, optionally, this first part 4 also comprises a tubular duct 49 adapted for receiving an additional rod intended to be temporarily implanted into the bone S for assisting the osteosynthesis technique (this tubular duct 49 is shown in dotted lines in FIGS. 2, 3 and 5).

This tubular duct 49 is herein arranged in the upper portion 41, through the other lateral edge 414 thereof and near the lower edge 413 thereof (intended to form the upper edge 21 of the guide window 2).

This tubular duct 49 has a longitudinal axis 49' that is directed parallel, or at least approximately parallel, to the above-mentioned lower edge 413 (FIG. 2).

This tubular duct 49 is hence directly arranged overlying the guide window 2 and is directed in such a manner that its longitudinal axis 49' is parallel to the plane 2' of the guide window 2 to position a rod helping in the guiding of the cut line (this "additional" rod 83 is schematically shown in FIG. 9).

This tubular duct 49 extends parallel to the plane defined by the upper edge 21 of the guide window 2, with an offset comprised between 0.5 and 3 mm with respect to this upper edge 21 (preferably of the order of 1 mm).

This tubular duct 49 also defines an angle comprised between 10° and 30° with respect to the general plane of the first part 4' (FIG. 4).

Second Part

The second part 5, illustrated in isolation in FIG. 6, also comprises several faces:
- two opposite faces: a rear face 51 and a front face 52,
- two lateral faces 53: a first lateral face 531 (on the right in FIG. 6) and a second lateral face 531 (on the left in FIG. 6), forming a lower portion of the lateral faces 13 of the surgical guide device 1, and
- two end faces: a proximal face 54 and a distal end 55.

The rear face 51 is intended to form a lower portion of the rear face 11 of the surgical guide device 1 (FIG. 3).

The front face 52 comprises a recess 521 intended to receive the lower portion 44 of the first part 4.

The proximal face 54 constitutes an upper edge of the second part 5, which is intended to form a portion of the lower edge 22 of the guide window 2 (herein a rear portion of this lower edge 22) herein in combination with the upper edge 443 of the lower portion 44 of the first part 4.

A location 541 dedicated to the guidance of a biplanar cutting may be provided at this proximal face 54 (visible in FIG. 10).

This location 541 is added to the surgical guide device 1 when the cut line comes into conflict with the tibial tuberosity. It is then necessary to protect the insertion of the patellar tendon by this method.

This location 541 is herein located on the opposite side with respect to the lateral opening 23.

This proximal face 54 also comprises, on the side of the lateral opening 23, spacer means 542 to maintain the spacing between the two edges 21, 22 of the guide window 2 (FIGS. 2 and 10).

These spacer means 542 consist for example of an integral stud equipping the proximal face 54 and coming into rest against the lower edge 413 of the first part 4.

The second part 5 comprises several through-orifices 56 that are adapted to receive elements temporarily implantable into the bone S and/or to guide a drilling of holes into this bone S.

Herein, this second part 5 comprises through-orifices 56, also called "distal through-orifices", which are intended in particular to serve as a guide for the drilling of holes into a distal fragment of the bone in order to facilitate the later assembly of the osteosynthesis plate.

These through-orifices 56 open through said rear 51 and front 52 faces of the second part 5.

These juxtaposed through-orifices 56 are at least two in number (herein three in number).

These through-orifices 56 extending in a virtual strip 56' intended to be directed approximately parallel with respect to the longitudinal axis S' of the bone (FIG. 1).

The first lateral face 531 of this second part 5 comprises tabs 57 intended to be positioned against the surface of the bone S, as developed hereinafter in relation with FIGS. 7 to 13.

These tabs 57 have a rear face that corresponds approximately to the anatomic surface of the bone intended to be covered by them; they have an ability of elastic deformation, so as to conform optimally the surface of the bone S.

These tabs 57 extend approximately parallel to the proximal face 54 and on the side of the rear face 51.

Herein, this second part 5 comprises two tabs:
- an upper tab 571, arranged along the proximal face 54, and
- a lower tab 572, arranged on the side of the distal face 55.

In particular, the upper tab 571 comprises an upper edge 5711 extending in the continuation of the proximal face 54 so as to help in forming the guide surface for the cut line.

Moreover, this second part 5 also comprises tubular ducts 58 adapted to receive rods intended to be temporarily implanted into the bone S for assisting the osteosynthesis technique.

A first, upper or proximal, tubular duct 581 (also called "upper barrel") is herein arranged through the upper tab 571.

This upper tubular duct 581 comprises a longitudinal axis 581' that is directed parallel, or at least approximately parallel, to the proximal face 54 (FIG. 2).

This longitudinal axis 581' is moreover advantageously directed parallel, or at least approximately parallel, to the longitudinal axis 49' of the tubular duct 49 of the first part 4.

This proximal tubular duct 581 is arranged directly underlying the guide window 2 and is directed in such a manner that its longitudinal axis 581' is parallel to the plane 2' of the guide window 2.

This proximal tubular duct 581 is adapted to guide an upper rod that is intended to help in guiding the cut line.

This proximal tubular duct 581 extends parallel to the plane defined by the lower edge 22 of the guiding window 2, with an offset comprised between 0.5 and 3 mm with respect to this lower edge 22 (preferably of the order of 1 mm).

This proximal tubular duct 581 also defines an angle comprised between 10° and 30° with respect to the general plane of the second part 5' (FIG. 4).

A second, lower or distal, tubular duct 582 (also called "lower barrel" or "first distal tubular duct" or "first lower tubular duct") is arranged through the lower tab 572.

This lower tubular duct 582 is directed in such a manner that its longitudinal axis 582' intersects the general plane 2' of the guide window 2 (FIG. 2).

This intersection point is intended to be located in the bulk of the bone, in particular at the opening site.

The intersection point makes it possible to localize a theoretical point located at a determined distance from the bone surface and from the plateau (for example, the theoretical point is located 10 to 11 mm from the external cortex).

This lower tubular duct 582 is intended to guide an ascending, lower rod serving as a cut stop and/or a hinge indication.

The direction of the longitudinal axis 582' of this lower tubular duct 582 may be defined by two angles:
- a first angle of inclination defined between the longitudinal axis 582' and the general plane 2' of the guide window 2, comprised between 40° and 70° (FIG. 2), and
- a second angle of inclination defined between the longitudinal axis 582' and the general plane of this second part 5', comprised between 35° and 70° (FIG. 4).

Figure 14:
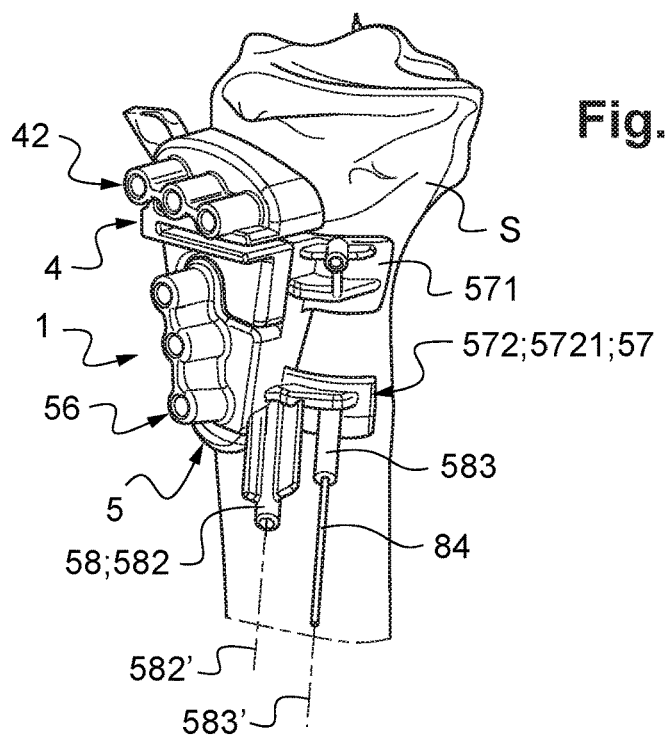
FIG. 14 is an overall and perspective view of a second surgical guide device according to the invention, placed against a patient's bone intended to undergo an opening wedge osteotomy technique, that is different from the device illustrated in FIGS. 1 to 13 by the presence of a third tubular duct adapted for guiding a second lower rod.
Figure 15:
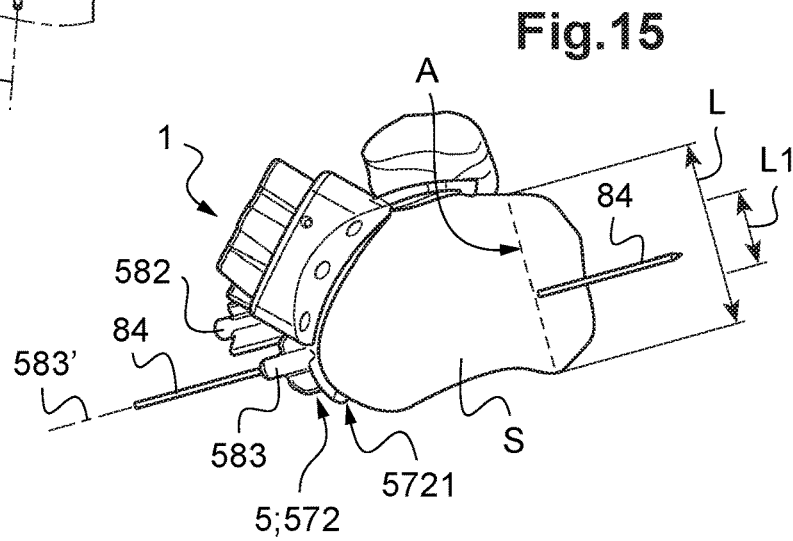
FIG. 15 is a general top view of the second surgical guide device according to the invention, with a transverse sectional plane passing through the bone and at the future hinge.

FIGS. 14 and 15 show a second surgical guide device according to the invention, that is a variant of the surgical device described hereinabove in relation with FIGS. 1 to 6.

The second surgical guide device 1 is different only by the presence of a third tubular duct 583 (also called "second lower tubular duct" or "second distal tubular duct"), arranged in the second part 5 for receiving a rod intended to be temporary implanted into the bone S for assisting the osteosynthesis technique.

The third, also lower or distal, tubular duct 583 (also called "second lower barrel") is herein arranged through the lower tab 572.

This third tubular duct 583 is herein arranged between the second tubular duct 582 and the free end 5721 of this lower tab 572. As an alternative, not shown, as a function of the primary location of the second tubular duct 582, the third tubular duct 583 can also be arranged between the first lateral face 531 of the second part 5 and the second tubular duct 582; this is for example the case when this second tubular duct 582 is offset and decentred to take into account the required change of tibial slope (indeed, the more we open posteriorward, the more the first rod will go anteriorward and hence close to the free end 5721 of the lower tab 572).

This third tubular duct 583 is oriented to that its longitudinal axis 583' intersects the general plane 2' of the guide window 2 (FIG. 2).

Its intersection point is intended to be located in the bulk of the bone, in particular at the opening site and still more precisely at the hinge.

The intersection point makes it possible to localize a theoretical point located at a determined distance from the bone surface and from the plateau (for example, the theoretical point is located 10 to 11 mm from the external cortex).

Figure 16:
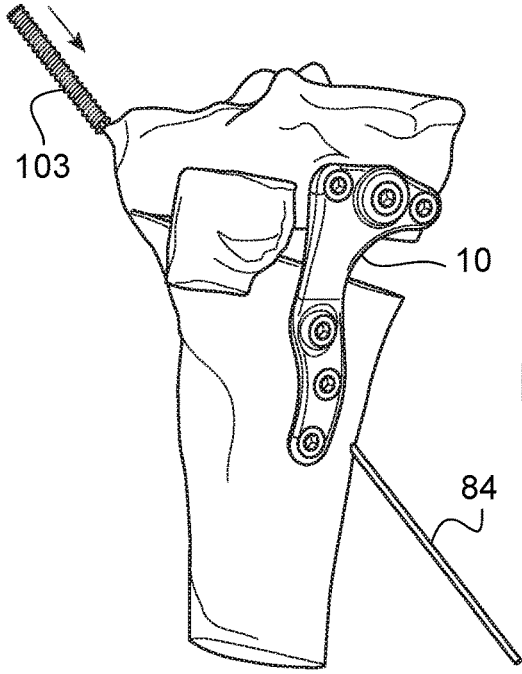
FIG. 16 illustrates a step of the surgical method implementing the second surgical guide device, i.e. the guiding of a cannulated screw by the second lower rod, for the insertion thereof into the hinge.

This third tubular duct 583 is intended to guide a second, ascending, lower rod. As illustrated in FIG. 16, the second lower rod is also useful to guide the insertion of a cannulated screw through the hinge.

The direction of the longitudinal axis 583' of this third tubular duct 583 is advantageously parallel to the longitudinal axis 582' of the second tubular duct 582.

Detachable Fastening Means

The two parts 4, 5 are assembled to each other through detachable fastening means 59, herein in the form of complementary fitting structures.

For that purpose, at its recess 521, the front face 51 of the second part 5 comprises dog points 591 (FIG. 6) intended to cooperate by fitting with complementary mortises (not visible) that are arranged at the rear face 441 of the distal portion 44 of the first part 4.

The second part 5 is also provided with lugs 592, for example in the form of spherical caps or conical studs (FIG. 6), which are judiciously distributed so as to cooperate by elastic fitting with complementary housings (not visible) equipping the first part 4.

Herein, these complementary lugs and housings are arranged on the opposite edges, on the one hand, of the aperture 444 of the first part 4 and, on the other hand, of the recess 521 of the second part 5.

Equipment for Opening Wedge Osteotomy Technique

As shown in FIG. 7 and following, the surgical guide device 1 is intended to be used in combination with a set of other elements for the implementation of the opening wedge osteotomy technique.

The corresponding equipment hence advantageously comprises:
- elements temporarily implantable into the bone, through the through-orifices 42, 56 of this surgical guide device 1, i.e. in particular rigid axes 7 (called "pins"),
- rods 8 temporarily implantable into the bone S, through the through-ducts 49, 58 of said surgical guide device 1,
- a cutting blade 9 (FIG. 9), associated with a surgical motor, to perform the cut line guided by the surgical guide device 1,
- an osteosynthesis plate 10 (FIGS. 11 to 13), provided with through-orifices 101 for receiving fastening screws 102 intended to be implanted into the bone S, and
- a set of screws 102 for the fastening to the bone S, intended to be inserted into the through-orifices 101 of the osteosynthesis plate 10 to fasten the latter to the surface of the bone S.

The osteosynthesis plate 10 is intended to be fastened to the two bone fragments, after the opening wedge osteotomy technique guided by the surgical guide device 1, so as to freeze the correction brought by the surgeon.

Such an osteosynthesis plate 10 is for example described in detail in the document FR2980967.

Figure 13:
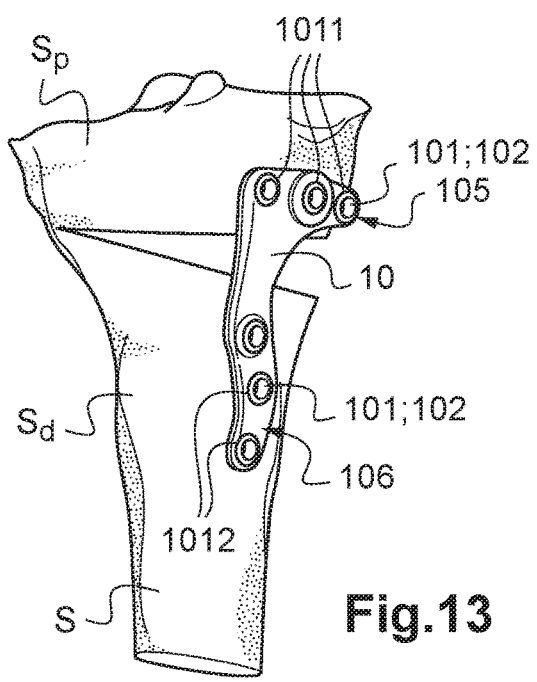

As described hereinafter in relation with FIG. 13, this osteosynthesis plate 10 is composed of two elongated portions, herein having together a general L-shape, i.e.:

a proximal part 105, intended to be positioned against a proximal fragment Sp of the bone S, and a distal part 106, intended to be positioned against a distal fragment Sd of this same bone S.

Each of these two parts 105, 106 is provided with a group of through-orifices 1011, 1012 for receiving fastening screws 102.

According to the invention, the arrangement of each group of through-orifices 42, 56 of the surgical guide device 1 corresponds to the arrangement of one the two groups of through-orifices 1011, 1012 of the osteosynthesis plate 1:

the arrangement of the through-orifices 42 of the first part 4 corresponds to the arrangement of the through-orifices 1011 of the proximal part 105 of the osteosynthesis plate 10, and the arrangement of the through-orifices 56 of the second part 5 corresponds to the arrangement of the through-orifices 1012 of the distal part 106 of the osteosynthesis plate 10.

Still according to the invention, the relative arrangement between the two groups of through-orifices 42, 56 of the surgical guide device 1 is function, on the one hand, of the correction intended to be applied during the opening wedge osteotomy technique and, on the other hand, of the relative arrangement of the two groups of through-orifices 1011, 1012 of the osteosynthesis plate 1.

Manufacturing of the Surgical Guide Device

The manufacturing of the surgical guide device 1 is advantageously custom made for the patient. This surgical guide device 1 hence advantageously consists of a patient specific instrument or "PSI".

The manufacturing of this surgical guide device 1, and as a corollary of its two constituent parts 4, 5, advantageously takes into account the following data:

anatomic data taken on the bone to be treated, advantageously obtained by a medical imaging technique (for example, scanner), data relating to the osteosynthesis plate 10 to be installed, in particular the final position of the locations of the screws 102 for the fastening of the osteosynthesis plate 10, and preoperative planning data, relating to the correction intended to be applied to this bone by the opening wedge osteotomy technique.

The method for obtaining a surgical guide device 1 according to the invention advantageously comprises the following steps:

a/ a step of simulating the correction intended to be applied to the bone S by an opening wedge osteotomy technique from the above-mentioned data, then b/ a step of manufacturing as such the surgical guide device 1, taking into account the correction data coming from the simulation step.

For the implementation of the simulation step, the invention advantageously proposes a preoperative planning tool in the form of a computer program intended to generate data for the manufacturing of the surgical guide device 1 on the basis of the above-mentioned data.

Herein, this computer program comprises program code means recorded on a computer-readable medium, comprising:

first program code means, for loading data relating to the correction intended to be applied to a bone by an opening wedge osteotomy technique, from anatomic data relating to the bone to be treated and from data relating to the final position of the screws for fastening the osteosynthesis plate to the bone, and second program code means, for generating manufacturing data relating to the surgical guide device 1, wherein said manufacturing data contain data relating, on the one hand, to the shape of the rear face 11 of the surgical guide device 1 and, on the other hand, to the arrangement of the through-orifices 42, 56 of the surgical guide device 1 taking into account said correction data and said screw final position data, when said computer program is executed by a computer.

The anatomic data of the bone to be treated consist for example of data coming from a scanner acquisition, from which a three-dimensional modelling of all the parts involved in the correction process is performed.

The correction data are provided by the surgeon, within the framework of its preoperative planning.

The final position of the screws and of the plate itself respects the common principles required for obtaining the mechanical performance sought for this material (in particular the anatomic positioning of the implant).

The second program code means advantageously consist of three-dimensional modelling means that are intended to generate the manufacturing data relating to the surgical guide device 1 as a "three-dimensional file" (or "3D file") that corresponds to a three-dimensional model operable by a three-dimensional printer.

As illustrated in relation with FIG. 7 and following, in said manufacturing data, the arrangement of the through-orifices 42, 56 of the surgical guide device 1 takes into account the planned opening wedge osteotomy technique and anticipates the final position of the screw locations in the osteosynthesis plate 10 placed so as to freeze the two bone fragments Sp and Sd.

The step of manufacturing the surgical guide device 1 consists of a step of additive manufacturing.

Surgical Method of Opening Wedge Osteotomy

A first step of the surgical method consists of a preparation step (FIGS. 7 and 8).

During said preparation step, the surgical guide device 1 (with its two parts 4 and 5 assembled to each other) is positioned so that the rear face 11 thereof comes into rest on the surface of the bone S, at the position of the future location of the osteosynthesis plate 10.

In the case of an internal tibial valgus opening wedge osteotomy, the surgical guide device 1 is positioned at the antero-internal part of the tibia.

In this case, as shown in FIG. 7, the tab 45 of the first part 4 then comes into rest on the insertion of the patellar tendon T, at the anterior tibial tuberosity; the tabs 57 of the second part 5 allow a good flattening of the surgical guide device 1 to the bone and a clearance compensation, so that the above-mentioned tab 45 is efficiently flattened to the posterior face of the patellar tendon T (position adjustment perpendicular to the axis S' of the bone S).

The upper protrusion 48 (located at the top of the surgical guide device 1) allows a first visual adjustment in height of the surgical guide device 1 (checking of the guide 1 altitude).

Finally, the upper rod 81 (or even the additional rod 83) makes it possible to control and validate this good positioning of the surgical guide device 1 thanks to a visualization with an image intensifier.

The upper rod 81, inserted into the second part 5 of the surgical guide device 1 and into the bone S through the upper tubular duct 581, temporarily freezes the surgical guide device 1 on the bone.

Optionally, the additional rod 83, inserted into the first part 4 of the surgical guide device 1 and into the bone S through the dedicated tubular duct 49, also helps in temporarily freezing the surgical guide device 1 on the bone.

This upper rod 81 (or even also the additional rod 83) also allows a checking of the altitude of the surgical guide device 1, in accordance with the planning file. For that purpose, the trajectory of this radio-opaque upper rod 81 (or even also of the additional rod 83) is superimposed to the theoretical trajectory determined during the simulation, such information appearing in the operative planning file provided to the surgeon.

The preparation step also comprises a "drilling" step, i.e. a step of forming holes into the bone S opposite each of the through-orifices 42, 56 of the surgical guide device 1.

For example, the holes are blind-holes at the (proximal) through-orifices 42 of the first part 4 and, on the other hand, are through-holes (bicortical) at the (distal) through-orifices 56 of the second part 5, respectively.

This surgical guide device 1 is then temporarily fastened against the surface of the bone S, by means of pins 7 placed through some at least of the through-orifices 42, 56 (FIG. 8).

This temporary fastening allows a robust holding of the surgical guide device 1 in order to ensure a very precise cutting within the guide window 2.

When this preparation step is finished, a step of osteotomy of the bone may be performed.

The beginning of the cutting is made thanks to the guide window 2, custom-positioned and dedicated to the previously known thickness of the cutting blade 9 (FIG. 9).

The upper rod 81 (or even also the additional rod 83) moreover allows following the trajectory of the cutting blade 9. This upper rod 81 (or even also the additional rod 83) allows visually checking that the good direction of cutting is not lost (for example, if the adjustment between the thickness of the blade and that of the window is too wide).

A lower rod 82 (also called "first lower rod 82") is then inserted into the bone, guided by the lower tubular duct 582 (FIG. 10).

This lower rod 82 is arranged so as to intersect the hinge of the osteotomy site (the site represents the empty space that will be created upon the tibia opening made possible by the saw line). In other words, this lower rod 82 intersects an axis of rotation A (FIG. 15), extending from the posterior part to the anterior part of the tibia, which represents the base line of the rotation about which the opening is made; this lower rod 82 further advantageously extends perpendicular, or at least approximately perpendicular, to this axis of rotation A.

This arrangement also provides a protection of the hinge during the opening movement, serving as a deformation "guide" and avoiding any breaking.

It also forms a cut stop but also the indication of the ideal position for the hinge.

According to the second embodiment, a second lower rod 84 may be inserted into the bone, guided by the third tubular duct 583 (FIGS. 14 to 16).

This second lower rod 84 is also arranged so as to intersect the hinge of the osteotomy site, near the intersection point of the first lower rod 82. In other words, here again, this second lower rod 84 intersects the axis of rotation A (FIG. 15) that represents the base line of the rotation about which the opening is made; this second lower rod 84 further advantageously extends perpendicular, or at least approximately perpendicular, to this axis of rotation A.

On this matter, this second lower rod 84 is advantageously strictly parallel to the first lower rod 82. This arrangement allows the second lower rod 84 to cross the axis of rotation of the hinge exactly in the same conditions as the first lower rod 82.

Preferably, the intersection point of the second lower rod 84 within the hinge is in a central portion L1 of the length L of this hinge (FIG. 15).

Such an arrangement aims at balancing, in the depth of the front plane, the location of the second lower rod 84 so that the screw slides on the latter and rebalances the fastening forces in case of breaking of the hinge.

For example, this central portion L1 (centred along the length of the hinge L) has a length corresponding to ⅓ (or even ¼, possibly ⅕) of the length of said hinge.

In a variant embodiment, the first lower rod 82 may be centred along the length of the hinge. In this case, the second lower rod 84 is offset along the length of this hinge, while remaining the closest possible of this first lower rod 82.

In practice, the second lower rod 84 is inserted after the cutting is finished. It may also be useful to recover the integrity of the hinge if the latter should break despite the presence of the first lower rod 82.

Moreover, the presence and visualization thereof beyond the cutting and beyond the lateral cortex makes it possible, if necessary, to come through external path, to thread the cannulated screw and to reinforce/synthetize the external hinge.

The first part 4 can then be removed after extraction of the holding pins 7 (FIG. 10).

The cutting blade 9 will be able to bear against the distal part 5 still fastened to the bone, and in particular to the upper tab 571 thereof, in order to continue following the ideal trajectory.

The operator can then get the hinge point by mechanically abutting against the first lower rod 82 that extends at the osteotomy site.

The hinge between the two bone fragments Sp, Sd is hence protected by this first lower rod 82 (or even also by the second lower rod 84) that passes through the cut line.

The first lower rod 82 (or even also the second lower rod 84) is left until the end of the operation when the plate is fully integral with the bone. Hence, all the intermediate handlings traumatizing the hinge, and that would risk to fragilize (or even break) it, are preserved thanks to the constant presence of this first lower rod 82 (or even also of the second lower rod 84).

It is to be noted that, once the second (distal) part 5 removed, it may slide along this first lower rod 82 (or even also the second lower rod 84) so that the (these) latter remain in position. The first lower rod 82 (or even also the second lower rod 84) hence plays a role of "stress absorber" and protects the bone from a risk of fracture, liable to create the separation of the two bone fragments.

Once the cut line ended, the second part 5 is also removed, while keeping the lower rod 82 (or even also the second lower rod 84) in unchanged position.

Figure 11:
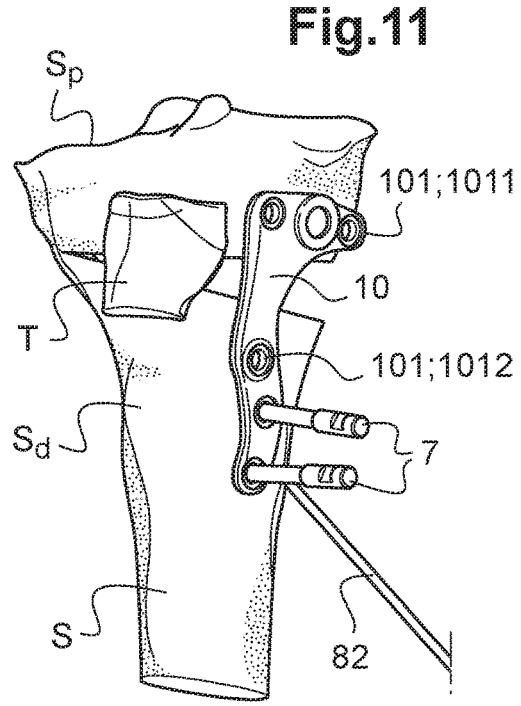

The osteosynthesis plate 10 is positioned by reinserting the pins 7 through the distal through-orifices 1012 thereof and so that they enter the holes of the distal fragment Sd obtained thanks to the second part 5 (FIG. 11).

The bone opening movement is performed by the operator. This operating movement is for example performed by means of a wedge inserted between the two bone fragments Sp and Sd (or any other suitable instrument, such as a Mehari clamp).

The correction is obtained in all the planes when the holes of the proximal bone fragment Sp (obtained by the first part 4) are opposite the proximal through-orifices 1011 of the osteosynthesis plate 10 (FIG. 11).

Indeed, as mentioned hereinabove, the relative arrangement between the two groups of through-orifices 42, 56 of the surgical guide device 1 takes into account, on the one hand, the correction intended to be applied during the opening wedge osteotomy technique, and on the other hand, the relative arrangement of the two groups of through-orifices 1011, 1012 of the osteosynthesis plate 10.

Figure 12:
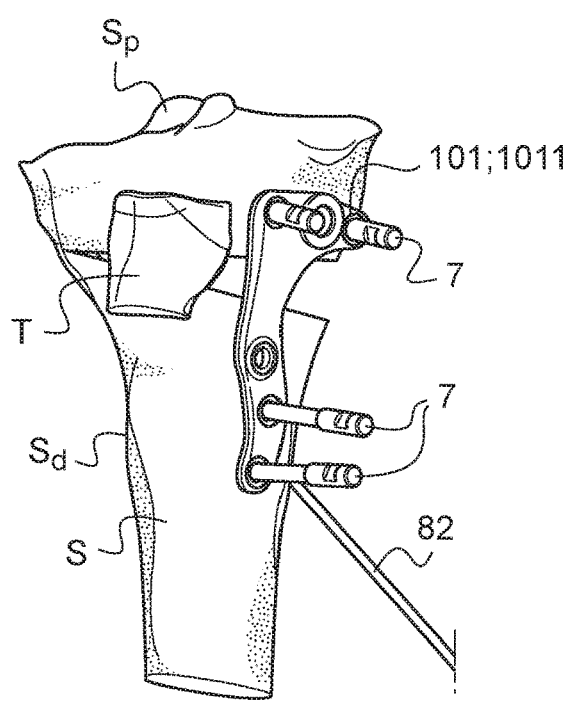

Pins 7 are then inserted through these proximal through-orifices 1011 to maintain the opening (FIG. 12).

The different fastening screws 102 are then successively inserted into the bone S, through the different orifices 101 of the osteosynthesis plate 10.

When the osteosynthesis plate 10 is definitively fastened, if he wants to, the operator can fill the obtained opening with, for example, solid or injectable synthetic bone substitutes, bone grafts (iliac grafts).

If he wants to, after the opening, the operation may also use the second lower rod 84 to guide the insertion of a cannulated screw 103 through the hinge (FIG. 16).

This cannulated screw 103 hence helps in maintaining the opening (or even also the bone substitute), in association with the osteosynthesis plate 10.

This cannulated screw 103 has also for vocation to reinforce the integrity of the hinge, and hence to further reduce the risk of postoperative breaking. It also allows taking part to the integrity of the hinge and hence to the good opening value defined by the surgical guide device 1.

Such a cannulated screw 103 may also be interesting within the framework of an intraoperative repair, in order to repair a hinge that would have broken despite the first lower rod 82 (after a too sudden movement, great opening, etc.).

Generally, the surgical guide device 1 hence helps the surgeon to make its operation in a precise and secure manner.

This surgical guide device has for interest to help the operator all along the opening wedge osteotomy operation (in particular for making the cut line and the opening), so as to precisely follow the preoperative planning.

This surgical guide device may be used to implement an opening wedge osteotomy technique on other bones, for example the distal femur, the wrist, the distal tibia.

This device also gives access to complex corrections in the three dimensions, with a continuous control of the operative process.

The invention claimed is:

1. A surgical guide device, intended to be placed against a patient's bone, for assisting an opening wedge osteotomy technique, said surgical guide device (1) comprising:
   a rear face (11) adapted to be positioned against a surface of said bone (S), and
   a window (2) for guiding a cut line intended to be made into said bone (S),
   wherein said guide window (2) is delimited by an upper edge (21) and a lower edge (22), arranged opposite to each other and spaced apart from each other,
   wherein said surgical guide device (1) further comprises two parts (4, 5) that are assembled to each other through detachable fastening means, said two parts (4, 5) being:
   a proximal part (4), having a lower edge (413) defining at least one portion of said upper edge (21) of said guide window (2), and
   a distal part (5), having an upper edge (54) defining at least one portion of said lower edge (22) of said guide window (2),
   wherein said proximal (4) and distal (5) parts are each provided with plural through-orifices (42, 56) opening through the rear face (11), adapted to receive elements (7) temporarily implantable into said bone (S) and/or adapted to guide a drilling of holes into said bone (S),
   wherein the distal part (5) comprises at least two distal tubular ducts (582, 583) adapted to guide the insertion of a rod within the bone (S), said at least two tubular ducts are arranged remote from the guide window (2) and that are directed in such a manner that their parallel longitudinal axes (582', 583') intersect a plane (2') of the guide window (2) in order to position a cut stop and/or hinge indication rod (82, 84) arranged so as to intersect the hinge of the osteotomy site, and
   wherein the device has two opposite lateral edges (13), at least one of which comprises at least one tab (45, 57) extending laterally therefrom adapted to be positioned against a surface of said bone (S), wherein said tab (45, 57) has an ability of elastic deformation, and wherein the at least two distal tubular ducts project from a front surface of the at least one tab;
   wherein the direction of each of the longitudinal axes (582', 583') of said distal tubular ducts (582, 583) is defined by two angles:
   a first angle of inclination defined in a first direction between the longitudinal axis (582', 583') and the plane (2') of the guide window (2), comprised between 40° and 70°, and
   a second angle of inclination defined in a second direction traversing the first direction between the longitudinal axes (582', 583') and a plane of the second part (5'), comprised between 35° and 70°.

2. The surgical guide device according to claim 1, wherein:
   the proximal part (4) comprises at least two through-orifices (42) of the plural through-orifices, juxtaposed and independent of each other, that extend in a virtual strip (42') intended to be directed transversally with respect to a longitudinal axis (S') of the bone (S), and
   the distal part (5) comprises at least two further through-orifices (56) of the plural through-orifices, juxtaposed and independent of each other, extending in a virtual strip (56') intended to be directed at least approximately parallel to the longitudinal axis (S') of the bone (S).

3. The surgical guide device according to claim 1, wherein the distal part (5) comprises at least one proximal tubular duct (581) that is adapted to guide the insertion of a rod within the bone (S),
   that is arranged directly underlying the guide window (2) and that is directed in such a manner that its longitudinal axis (581') is parallel to the plane (2') of the guide window (2) in order to position a rod (81) helping in the guiding of the cut line.

4. The surgical guide device according to claim 1, wherein the proximal part (4) is provided with an upper protrusion (48), advantageously intended to help a practitioner to correctly position the surgical guide device (1) at a good distance with respect to a tibial plateau of a patient.

5. The surgical guide device according to claim 1, comprising a plastic material adapted to the additive manufacturing.

6. Equipment for implementing an opening wedge osteotomy technique, comprising:
   a surgical guide device (1) according to claim 1,
   elements (7) intended to be temporarily implantable into said bone (S), through the through-orifices (42, 56) of said surgical guide device (1), rods (8) intended to be temporarily implantable into said bone (S), through the at least two tubular ducts (582, 583) of said surgical guide device (1), notably a cut stop and/or hinge indication rod (82, 84) arranged so as to intersect a hinge of an osteotomy site, a cutting blade (9), for making the cut line guided by the surgical guide device (1), an osteosynthesis plate (10) provided with two groups of through-orifices (1011, 1012), a proximal one and a distal one, each of said groups (1011, 1012) being intended to receive fastening screws (102) intended to be implanted into one of the two bone fragments, a set of screws (102) for the fastening to the bone (S), intended to be inserted through the through-orifices (1011, 1012) of said osteosynthesis plate (10) to fasten the latter to the surface of the bone (S), wherein the arrangement of the through-orifices (42) of the proximal part (4) corresponds to the arrangement of the proximal through-orifices (1011) of the osteosynthesis plate (10), wherein the arrangement of the through-orifices (56) of the distal part (5) corresponds to the arrangement of the distal through-orifices (1012) of the osteosynthesis plate (10), and wherein the relative arrangement between the two groups of through-orifices (42, 56) of the surgical guide device (1) is function of the correction intended to be applied during the opening wedge osteotomy technique and of the relative arrangement of the two groups of through-orifices (1011, 1012) of the osteosynthesis plate (10).

7. A method for obtaining a surgical guide device according to claim 1, comprising:

a) a step of simulating a correction intended to be applied to a bone (S) by an opening wedge osteotomy technique from the below-mentioned data:

anatomic data taken on the bone (S) to be treated, data relating to the osteosynthesis plate (10) to be installed, and preoperative planning data, relating to the correction intended to be applied to the bone (S) by the opening wedge osteotomy technique, and b) a step of manufacturing said surgical guide device (1), taking into account the correction data coming from said simulation step.

8. The method according to claim 7, wherein the step of manufacturing said surgical guide device (1) consists of a step of additive manufacturing.

9. Equipment for implementing an opening wedge osteotomy technique, comprising:

a cutting blade (9), for making a cut line, an osteosynthesis plate (10) provided with two groups of through-orifices (1011, 1012), a proximal one and a distal one, each of said groups (1011, 1012) being intended to receive fastening screws (102) intended to be implanted into one of the two bone fragments, a surgical guide device, intended to be placed against a patient's bone, for assisting an opening wedge osteotomy technique, rods (8) temporarily implantable into said bone (S), through through-ducts (58) of said surgical guide device (1), wherein said surgical guide device (1) comprises:

a rear face (11) adapted to be positioned against a surface of said bone (S), a window (2) for guiding a cut line intended to be made into said bone (S), wherein said guide window (2) is delimited by an upper edge (21) and a lower edge (22), arranged opposite to each other and spaced apart from each other, and two parts (4, 5), said two parts (4, 5) being:

a proximal part (4) and a distal part (5) assembled to each other through detachable fastening means, said two parts (4, 5) being:

a proximal part (4), having a lower edge (413) defining at least one portion of said upper edge (21) of said guide window (2), and a distal part (5), having an upper edge (54) defining at least one portion of said lower edge (22) of said guide window (2), wherein said proximal (4) and distal (5) parts are each provided with several through-orifices (42, 56) opening through the rear face (11), adapted to receive elements (7) temporarily implantable into said bone (S) and/or adapted to guide a drilling of holes into said bone (S), wherein the distal part (5) comprises at least two distal tubular ducts (582, 583) adapted to guide the insertion of a rod within the bone (S), said at least two tubular ducts are arranged remote from the guide window (2) and that are directed in such a manner that their parallel longitudinal axes (582', 583') intersect a plane (2') of the guide window (2) in order to position a cut stop and/or hinge indication rod (82, 84) arranged so as to intersect the hinge of the osteotomy site, and wherein the device has two opposite lateral edges (13), at least one of which comprises at least one tab (45, 57) extending laterally therefrom adapted to be positioned against a surface of said bone (S), wherein said tab (45, 57) has an ability of elastic deformation, and wherein the at least two distal tubular ducts project from a front surface of the at least one tab;

wherein the direction of each of the longitudinal axes (582', 583') of said distal tubular ducts (582, 583) is defined by two angles:

a first angle of inclination defined in a first direction between the longitudinal axis (582', 583') and the plane (2') of the guide window (2), comprised between 40° and 70°, and a second angle of inclination defined in a second direction traversing the first direction between the longitudinal axes (582', 583') and a plane of the second part (5'), comprised between 35° and 70°.

10. The equipment for implementing an opening wedge osteotomy technique, according to claim 9, wherein the distal part comprises at least two distal tubular ducts that are arranged remote from the cut line and that are directed in such a manner that their respective longitudinal axes intersect the plane of the guide window in order to each position a cut stop and/or hinge indication rod.

11. The equipment for implementing an opening wedge osteotomy technique, according to claim 9, comprising a cannulated screw (103) guided on a hinge indication rod and intended to be inserted through the hinge.

12. The equipment for implementing an opening wedge osteotomy technique, according to claim 9, wherein the distal part (5) comprises a proximal tubular duct (581) that is adapted to guide the insertion of a rod within the bone (S), directed in such a manner that its longitudinal axis (581') is parallel to the plane of the cut line in order to position a rod (81) helping in the guiding of the cut line.

* * * * *